United States Patent
Mansour et al.

(10) Patent No.: US 11,204,317 B2
(45) Date of Patent: Dec. 21, 2021

(54) TOMOGRAPHIC IMAGING SYSTEM

(71) Applicant: Mitsubishi Electric Research Laboratories, Inc., Cambridge, MA (US)

(72) Inventors: Hassan Mansour, Boston, MA (US); Ajinkya Kadu, Utrecht (NL); Petros Boufounos, Winchester, MA (US); Dehong Liu, Lexington, MA (US)

(73) Assignee: Mitsubishi Electric Research Laboratories, Inc., Cambridge, MA (US)

( * ) Notice: Subject to any disclaimer, the term of this patent is extended or adjusted under 35 U.S.C. 154(b) by 403 days.

(21) Appl. No.: 16/285,344

(22) Filed: Feb. 26, 2019

(65) Prior Publication Data

US 2020/0271577 A1  Aug. 27, 2020

(51) Int. Cl.
*G06T 11/00* (2006.01)
*A61B 8/13* (2006.01)
(Continued)

(52) U.S. Cl.
CPC ........... *G01N 21/47* (2013.01); *A61B 8/13* (2013.01); *G01N 23/046* (2013.01); *G06T 11/005* (2013.01); *G06T 11/006* (2013.01); *G01N 2021/1787* (2013.01); *G01N 2201/126* (2013.01); *G06T 2211/424* (2013.01)

(58) Field of Classification Search
None
See application file for complete search history.

(56) References Cited

U.S. PATENT DOCUMENTS

| 6,587,540 B1* | 7/2003 | Johnson | A61B 5/4312 378/4 |
| 2007/0091301 A1* | 4/2007 | Volker | G01N 15/02 356/235 |

(Continued)

OTHER PUBLICATIONS

Zahra Turani, Emad Fatemizadeh, Quiyun Xu, Steven Daveluy, Darius Mehregan, Mohammadresza Nasiriavanaki; Refractive index correction in optical coherence tomography images of multilayer tissues; Jul. 10, 2018; SPIE; vol. 23(7); p. 1. (Year: 2018).*

(Continued)

*Primary Examiner* — Joni Hsu
(74) *Attorney, Agent, or Firm* — Gennadiy Vinokur; Hironori Tsukamoto

(57) ABSTRACT

A tomographic imaging system receives measurements at a set of frequencies of a wavefield scattered by an internal structure of an object, recursively reconstructs an image of the internal structure of the object until a termination condition is met, and renders the reconstructed image. For a current iteration, the system adds a frequency to a previous set of frequencies used during a previous iteration to produce a current set of frequencies, such that the added frequency is higher than any frequency in the previous set of frequencies, and reconstructs a current image of the internal structure of the object that minimizes a difference between a portion of the scattered wavefield measured at the current set of frequencies and a wavefield synthetized from the current image. A previous image determined during the previous iteration initializes the reconstruction of the current image.

18 Claims, 12 Drawing Sheets

(51) Int. Cl.
*G01N 23/046* (2018.01)
*G01N 21/47* (2006.01)
*G01N 21/17* (2006.01)

(56) References Cited

U.S. PATENT DOCUMENTS

| | | | | |
|---|---|---|---|---|
| 2015/0129768 A1* | 5/2015 | Koizumi | A61B 5/0507 | 250/341.1 |
| 2015/0279082 A1* | 10/2015 | Anderson | G01S 7/046 | 345/424 |
| 2016/0025878 A1* | 1/2016 | Shin | G01V 1/282 | 367/7 |
| 2016/0135694 A1* | 5/2016 | van Dorp | A61B 5/0507 | 600/430 |
| 2016/0320506 A1* | 11/2016 | Almuhaidib | G01V 1/364 | |

OTHER PUBLICATIONS

Ren S, Dong F; Interface and permittivity simultaneous reconstruction in electrical capacitance tomography based on boundary and finite-elements coupling method; Jun. 28, 2016; The Royal Society publishing; p. 1. (Year: 2016).*

* cited by examiner

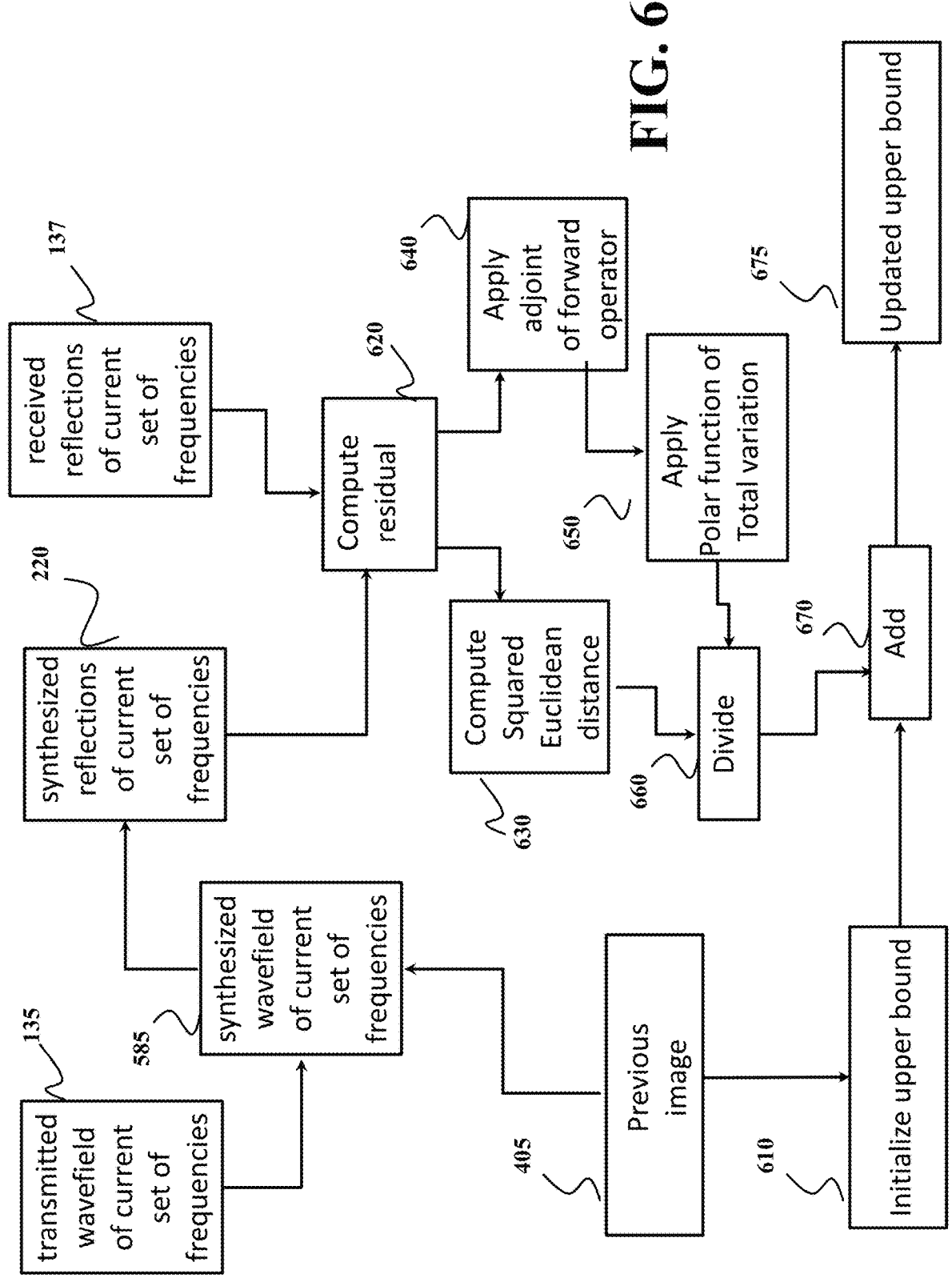

ND IMAGING SYSTEM

TOMOGRAPHIC IMAGING SYSTEM

TECHNICAL FIELD

This invention relates to tomography, and more specifically to a tomographic imaging system reconstructing an image of internal structure of an object by solving an inverse scattering problem.

BACKGROUND

Knowledge of the spatial distribution of the dielectric permittivity within a material is important for many applications such as microwave imaging, biomicroscopy, medical imaging, through-the-wall imaging (TWI), infrastructure monitoring, and seismic imaging. In particular, determination of permittivity enables the visualization of the internal structure of the material and characterization of its physical properties. For example, in microwave imaging permittivity provides the structure and properties of objects in the material. In biomicroscopy, the permittivity allows to visualize the internal cell structure in three-dimensions. In TWI, the permittivity allows to learn the dielectric properties of the wall and to use that information to compensate for the delay of the signal propagating through the wall.

In a typical scenario, a transmitter emits a signal such as an electromagnetic (EM), light or acoustic pulse, which propagates through the material, reflects off various structures inside the material, and propagates to a receiver antenna array. The composition of the material is then visualized by numerically generating an image that represents the distribution of the permittivity in the material. Example of such an image include an image of refractive indices of material inside the object. However, depending on the type of material, the received reflections often resulted from the multiple reflections and/or refractions of the propagating pulse due to multiple scattering from the structures in the material, which results in either artifacts that clutter the reconstructed image.

Accordingly, there is a need for a method determining an image of a distribution of permittivity of a material that accounts for the multiple scattering of a probing pulse propagating through the material. However, the multiple scattering of the pulse affects the pulse in a non-linear manner, making such a determination more difficult. See, e.g., U.S. Pub. 2017/0261538.

SUMMARY

It is an object of some embodiments to reconstruct an image of internal structure of an object probed with electromagnetic or acoustic waves of finite bandwidth to measure the scattered wavefield around the object. An incident wavefield propagating inside the object induces multiple scattering waves on boundaries of material inside the object. Consequently, the scattered waves contain information about the spatial distribution of the material properties, which has led to applications in numerous fields, such as, non-destructive testing, optical tomography, geophysical imaging, ground penetrating radar, and medical imaging. For example, the spatial distribution of the material properties in the reconstructed image can be represented by refractive indices of material inside the object and/or distribution of permittivity of material inside the object.

Some embodiments are based on recognition that such an image can be reconstructed by solving an inverse scattering problem. Indeed, the input wavefield of the probing pulse is known, and the scattered wavefield can be measured. The inverse scattering problem aims to find the distribution of the permittivity of the material that transforms the known input wavefield into the measured reflections of the scattered wavefield. However, the inverse scattering problem is ill-posed and difficult to solve.

In addition, two acquisition modes exist in inverse scattering: transmission mode, where the transmitters and receivers are located on opposite sides of the material, and reflection mode, where the transmitters and receivers are located on the same side of the object. The reflection setup generally arises due to a limitation that allows accessing only one side of the material, as in the case of underground imaging. To that end, the reflection setup is effective in some applications, but results in the reflection tomography scenario where the inverse scattering problem is severely ill-posed since the measured wavefields contain far less spatial frequency information about the object. To that end, it is an object of one embodiment to provide method and system suitable for reflection tomographic imaging.

Some embodiments are based on recognition that the inverse scattering problem for reconstructing the internal structure of the object can be addressed by minimizing a cost function indicative of a difference between the scattered wavefield and a wavefield synthetized from the image of the internal structure of the object. However, the input wavefield is scattered differently for different frequencies complicating the scattered wavefield and making the cost function highly non-linear with multiple local minima. Hence, the inverse scattering problem minimizing such a cost function is a challenging problem that to the best of our knowledge has not been fully addressed.

However, some embodiments are based on realization that the low frequency component of the incident wavefield is capable of penetrating further into the material of the object and exhibits weaker interaction with the internal structure of the object compared to higher frequency components. As a result of the weaker interaction, fewer scattering events occur during the penetration of low frequency wavefields. Consequently, the measurement mismatch cost function corresponding to the low frequencies has fewer local minima compared to higher frequencies. The low frequency measurements contain less spatial detail compared to the higher frequency measurements, but they can serve to initialize optimization of the inverse scattering problem with the higher frequency measurements.

To that end, some embodiments disclose an incremental frequency inversion method. For example, in some embodiments, the incremental frequency inversion method recursively reconstructs an image of the internal structure of the object until a termination condition is met. For a current iteration, the method adds a frequency to a previous set of frequencies used during a previous iteration to produce a current set of frequencies and reconstructs a current image of the internal structure of the object that minimizes a difference between a portion of the scattered wavefield measured at the current set of frequencies and a wavefield synthetized from the current image. The added frequency is higher than any frequency in the previous set of frequencies. In such a manner, frequencies are added incrementally to the inverse scattering problem. In addition, a previous image determined during the previous iteration initializes the reconstruction of the current image. This initialization incrementally guides the solution of the inverse scattering problem toward a global minimizer.

The incremental frequency inversion method does not require a smooth initial model of the image to be reconstructed. In contrast, the incremental frequency inversion method derives such a model from low frequency measurements. In effect, the incremental frequency inversion method allows to reconstruct an image of the internal structure of the object with a practical resolution and accuracy without a necessity for using prior information about the image.

Accordingly, one embodiment discloses 1a tomographic imaging system, including an input interface to receive measurements at a set of frequencies of a wavefield scattered by an internal structure of an object; a processor configured to recursively reconstruct an image of the internal structure of the object until a termination condition is met, wherein, for a current iteration, the processor is configured to add a frequency to a previous set of frequencies used during a previous iteration to produce a current set of frequencies, wherein the added frequency is higher than any frequency in the previous set of frequencies; and reconstruct a current image of the internal structure of the object that minimizes a difference between a portion of the scattered wavefield measured at the current set of frequencies and a wavefield synthetized from the current image, wherein a previous image determined during the previous iteration initializes the reconstruction of the current image; and an output interface configured to render the reconstructed image.

Another embodiment discloses a tomographic imaging method that uses a processor coupled with stored instructions implementing the method, wherein the instructions, when executed by the processor carry out steps of the method, including receiving measurements at a set of frequencies of a wavefield scattered by an internal structure of an object; reconstructing recursively an image of the internal structure of the object until a termination condition is met, wherein, for a current iteration, the method includes adding a frequency to a previous set of frequencies used during a previous iteration to produce a current set of frequencies, wherein the added frequency is higher than any frequency in the previous set of frequencies; and reconstructing a current image of the internal structure of the object that minimizes a difference between a portion of the scattered wavefield measured at the current set of frequencies and a wavefield synthetized from the current image, wherein a previous image determined during the previous iteration initializes the reconstruction of the current image; and rendering the reconstructed image.

Yet another embodiment discloses a non-transitory computer readable storage medium embodied thereon a program executable by a processor for performing a method, the method including receiving measurements at a set of frequencies of a wavefield scattered by an internal structure of an object; reconstructing recursively an image of the internal structure of the object until a termination condition is met, wherein, for a current iteration, the method including: adding a frequency to a previous set of frequencies used during a previous iteration to produce a current set of frequencies, wherein the added frequency is higher than any frequency in the previous set of frequencies; and reconstructing a current image of the internal structure of the object that minimizes a difference between a portion of the scattered wavefield measured at the current set of frequencies and a wavefield synthetized from the current image, wherein a previous image determined during the previous iteration initializes the reconstruction of the current image; and rendering the reconstructed image.

BRIEF DESCRIPTION OF THE DRAWINGS

FIG. 6 shows a block diagram of a method for updating an upper bound 610 $\tau$ on a total variation penalty function according to one embodiment.

DETAILED DESCRIPTION

Figure 1:
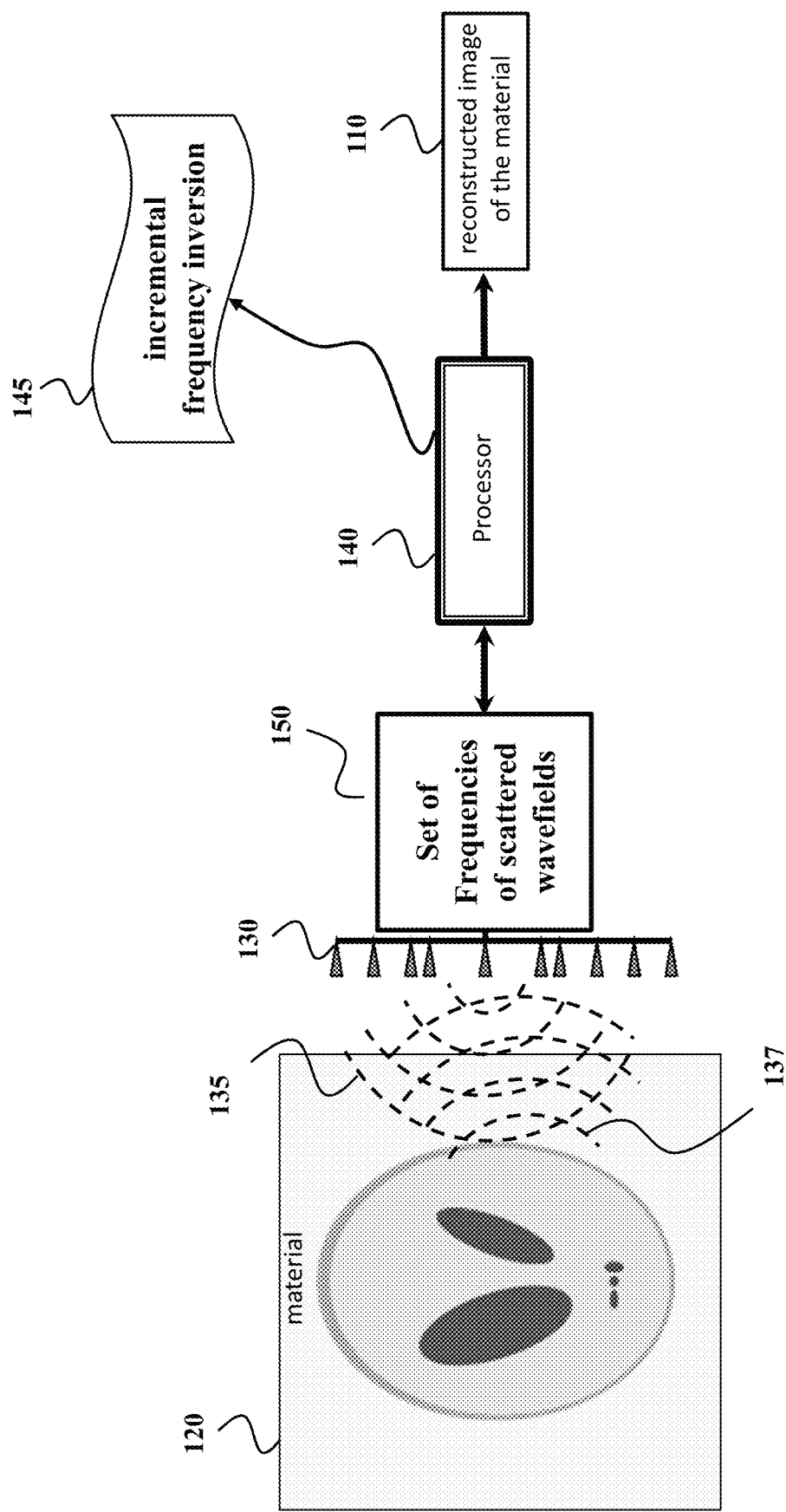
FIG. 1 shows a block diagram of a tomographic imaging tomographic imaging system for determining an image 110 of an internal structure of the object 120 according to one embodiment.

FIG. 1 shows a block diagram of a tomographic imaging tomographic imaging system for determining an image 110 of an internal structure of the object 120 according to one embodiment. The image of the internal structure can be represented, for example, by an image of refractive indices of material inside the object, an image showing distribution of permittivity of material inside the object, and combination thereof. The tomographic imaging system includes and/or is operatively connected to at least one transceiver 130 to propagate a pulse of wave 135 through the material 120 and to receive a set of echoes 137 resulted from scattering the pulse by different portions of the material.

For example, the transceiver can include at least one transmitter that transmits the pulse through the material, such that the pulse scattered by the material produces the set of echoes 137. The pulse can be any type of electromagnetic, acoustic, or optical waves, such as one or combination of a microwave pulse, a radar pulse, a laser pulse, an ultrasound pulse, an acoustic pulse. The transceiver can also include at least one receiver arranged at a predetermined location with respect to the transmitter for receiving the set of echoes 137. According to different embodiments, the tomographic imaging system can produce a two- or three-dimensional image of the material, where each location in the image provides the value of the dielectric permittivity for a portion of material corresponding to that location.

The tomographic imaging system also includes a processor 140 operatively connected with the transceiver 130 to determine the image 110 based on the set of echoes 137. In order to reconstruct the image of the material 110 despite the multiple scattering, the processor separates the reconstruction into several stages by operating on a set of frequencies 150 of the scattered wavefields. The processor implements an incremental frequency inversion method 145. For example, in some embodiments, the incremental frequency inversion method 145 recursively reconstruct an image of the internal structure of the object 110 for higher frequencies until a termination condition is met.

Figure 2A:
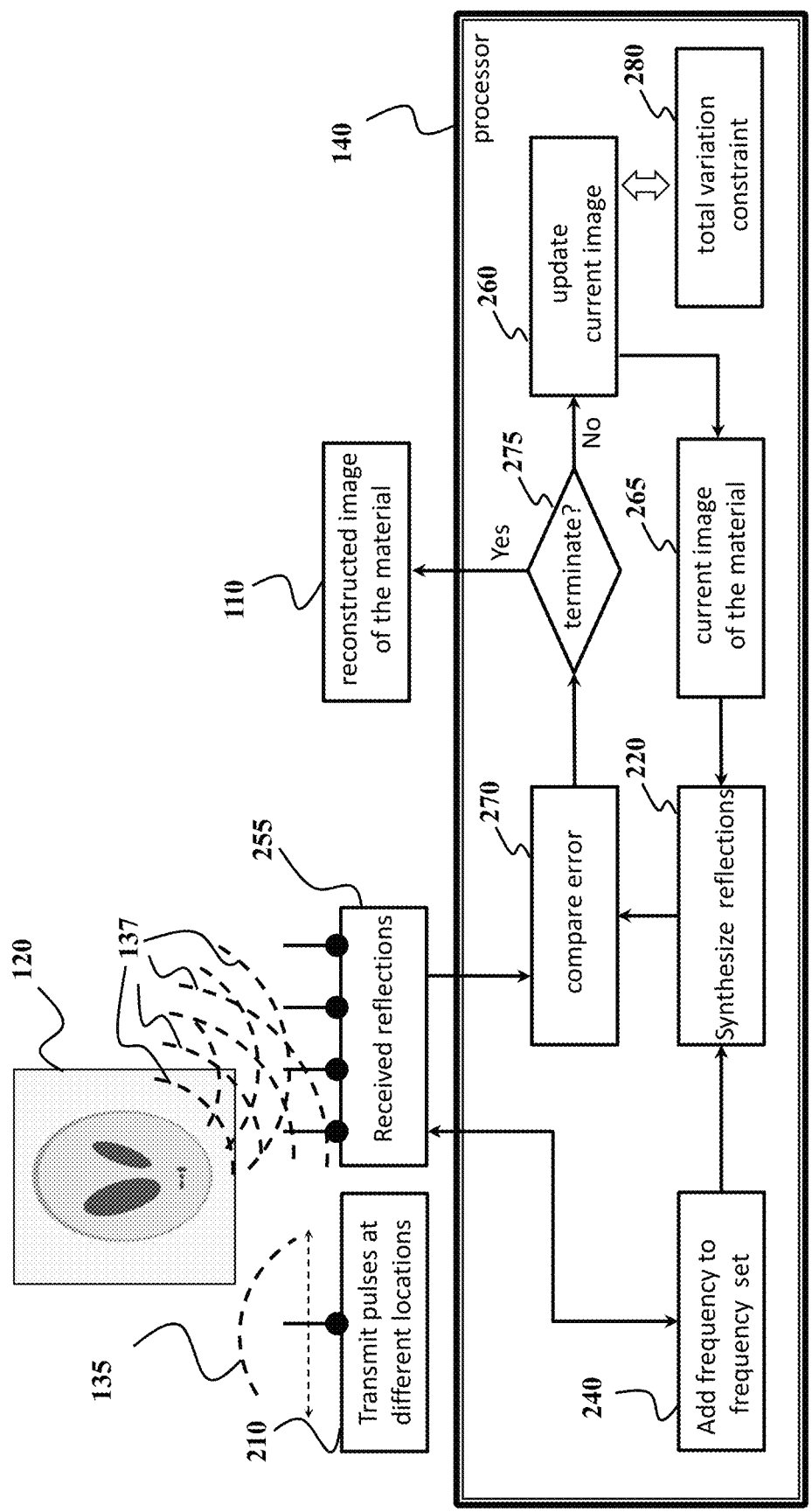
FIG. 2A shows a block diagram of a method for determining an image of an internal structure of an object according to some embodiments.

FIG. 2A shows a block diagram of a method for determining an image of an internal structure of an object according to some embodiments. The method can be implemented using the processor 140. For example, the method can be implemented by the processor executing a program embodied on a non-transitory computer readable storage medium.

The method propagates 210 a pulse of wave 135 through the material to receive a set of echoes 137 resulted from scattering the pulse by different portions of the material. The pulse of wave 135 spans across a frequency band including a set of frequencies. For example, the set of frequencies is a product of quantization of a frequency band of the pulse 135. In one embodiment, the quantization is performed with resolution proportional to the length of the time by which the echoes were sampled. This resolution allows to reconstruct the necessary details of the image such that the frequency separation of the quantization bins is small enough that adjacent frequency bins contain overlapping information on the image detail. In another embodiment, the resolution is selected based on computational power of the processor 140. For example, a processor with limited memory would require that the quantization bins be larger, resulting in a smaller number of frequencies.

According to the principles of the incremental frequency inversion 145, the method is not aiming to reconstruct the image jointly for all frequencies at once. In contrast, the method reconstructs the image for a subset of frequency and incrementally adds the frequency in the subset to further refine the image. Eventually, the method processes all frequency. However, in the incremental frequency inversion 145, the previously determined image serves as a prior for reconstruction of the next image to improve the quality of image reconstruction.

To that end, the method incrementally adds 240 a frequency from the received reflections 255 to a current set of frequencies and, for each iteration, performs the image reconstruction only for the frequencies in the current set of frequencies. To reconstruct a current image of the internal structure of the object, the method minimizes a difference between a portion of the scattered wavefield measured at the current set of frequencies and a wavefield synthesized from the current image. In some embodiments, the method uses a current image of the material 265, i.e., the previous image reconstructed during the previous iteration, to synthesize a wavefield 220 that is compared with the received reflections 255. The error between the received reflections 255 and the synthesized wavefield 220 is compared 270 such that when the error is smaller than a threshold, the current image 265 is output as the reconstructed image of the material 110. Otherwise, the current image is updated 260 in such a way that minimizes the error. Additionally, or alternatively, the method terminates 275 when all frequencies in the set of frequencies are processed. Optionally, some embodiments use different regularizes, such as a total variation constraint 280 to the update current image.

Figure 2B:
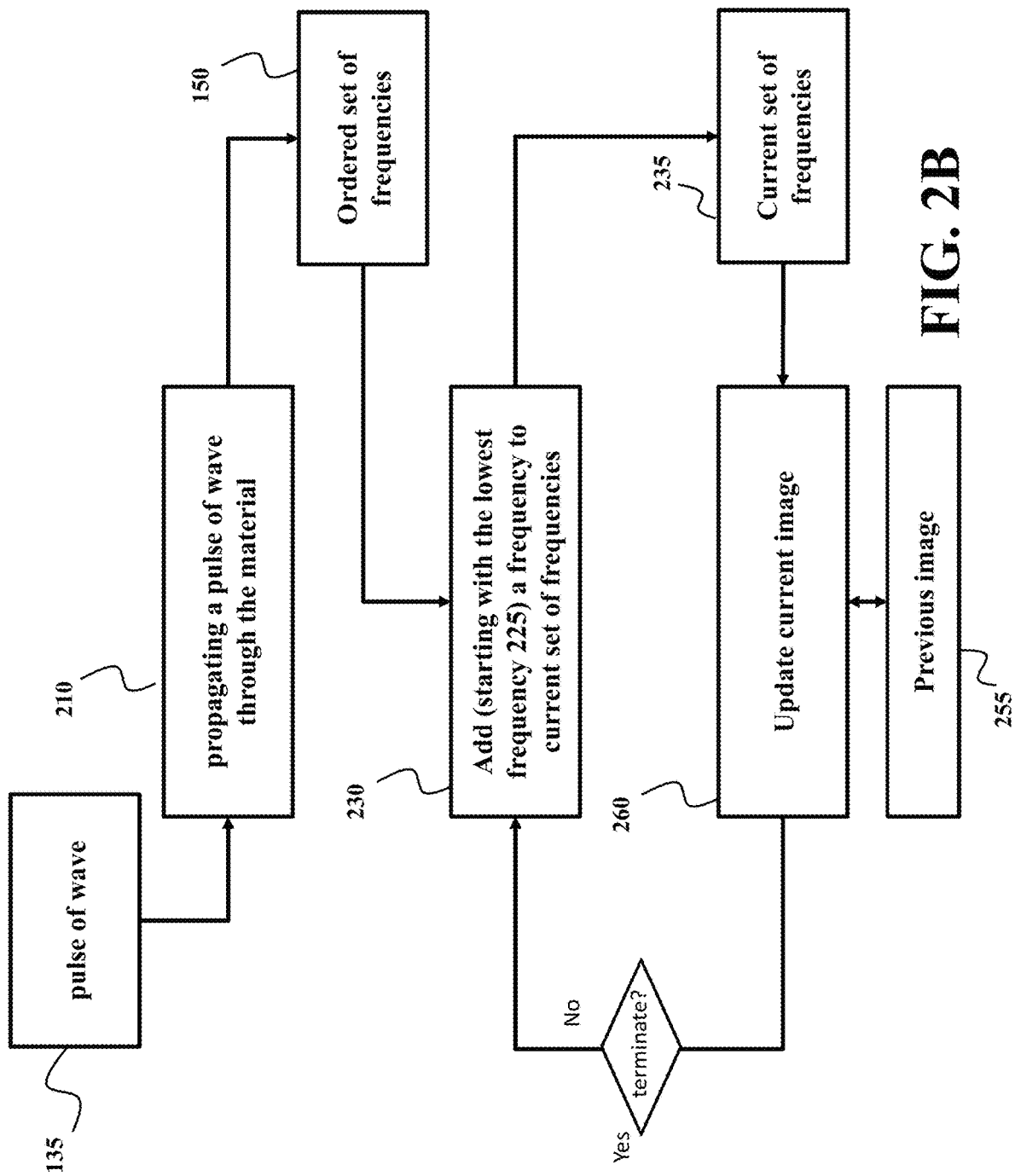
FIG. 2B shows a schematic of implementation of the method of FIG. 2A according to one embodiment.

FIG. 2B shows a schematic of implementation of the method of FIG. 2A according to one embodiment. The method can be implemented using the processor 140. The processor requests to propagate 210 a pulse of wave through the material. For example, the processor commands to transmit 250 the pulse 135 through the material, such that the pulse scattered by the material produces the set of echoes 137. Also, the processor receives 255 the set of echoes 137. The processor can also request to transform, the received reflections into a digital signal using an analog-to-digital converter and to record amplitude and/or other properties of the digital signal.

In some embodiments the processor organizes the received reflections into an ordered set of frequencies 150 where the frequencies are ordered from the lowest frequency to the highest frequency. For example, the processor initializes the current set of frequencies 235 to by placing 225 the lowest frequency in the current set of frequencies. Then for each iteration, the processor updates 260 the current image based on the wavefield in the current set of frequencies and check a termination condition which terminates the process when all frequencies in the ordered set of frequencies 150 have been included in the current set of frequencies. In the subsequent iterations, the processor adds 220 a frequency from the ordered set of frequencies 150 such that the added frequency is higher than any frequency in the previous set of frequencies.

Some embodiments are based on recognition that the inverse scattering problem for reconstructing the internal structure of the object can be addressed by minimizing a cost function indicative of a difference between the measured reflections and a reflections synthetized from the image of the internal structure of the object. However, the input wavefield is scattered differently for different frequencies complicating the scattered wavefield and making the cost function highly non-linear with multiple local minima. Hence, the inverse scattering problem minimizing such a cost function is a challenging problem that to the best of our knowledge has not been fully addressed.

However, some embodiments are based on realization that the low frequency component of the incident wavefield is capable of penetrating further into the material of the object and exhibits weaker interaction with the internal structure of the object compared to higher frequency components. As a result of the weaker interaction, fewer scattering events occur during the penetration of low frequency wavefields. Consequently, the measurement mismatch cost function corresponding to the low frequencies has fewer local minima compared to higher frequencies. The low frequency measurements contain less spatial detail compared to the higher frequency measurements, but they can serve to initialize optimization of the inverse scattering problem with the higher frequency measurements.

Some embodiments are based on understanding that it is easier to process each frequency separately, and later to reconstruct the image together by stitching images of different frequencies in a frequency domain. However, this option is not suitable for reconstruction of internal structure of the object due to interdependencies of scattered wavefield on different frequency. To that end, some embodiments reconstruct the image jointly for multiple frequencies. However, the frequencies are added incrementally to gradually initialize reconstruction until all frequencies are joined.

Figure 3:
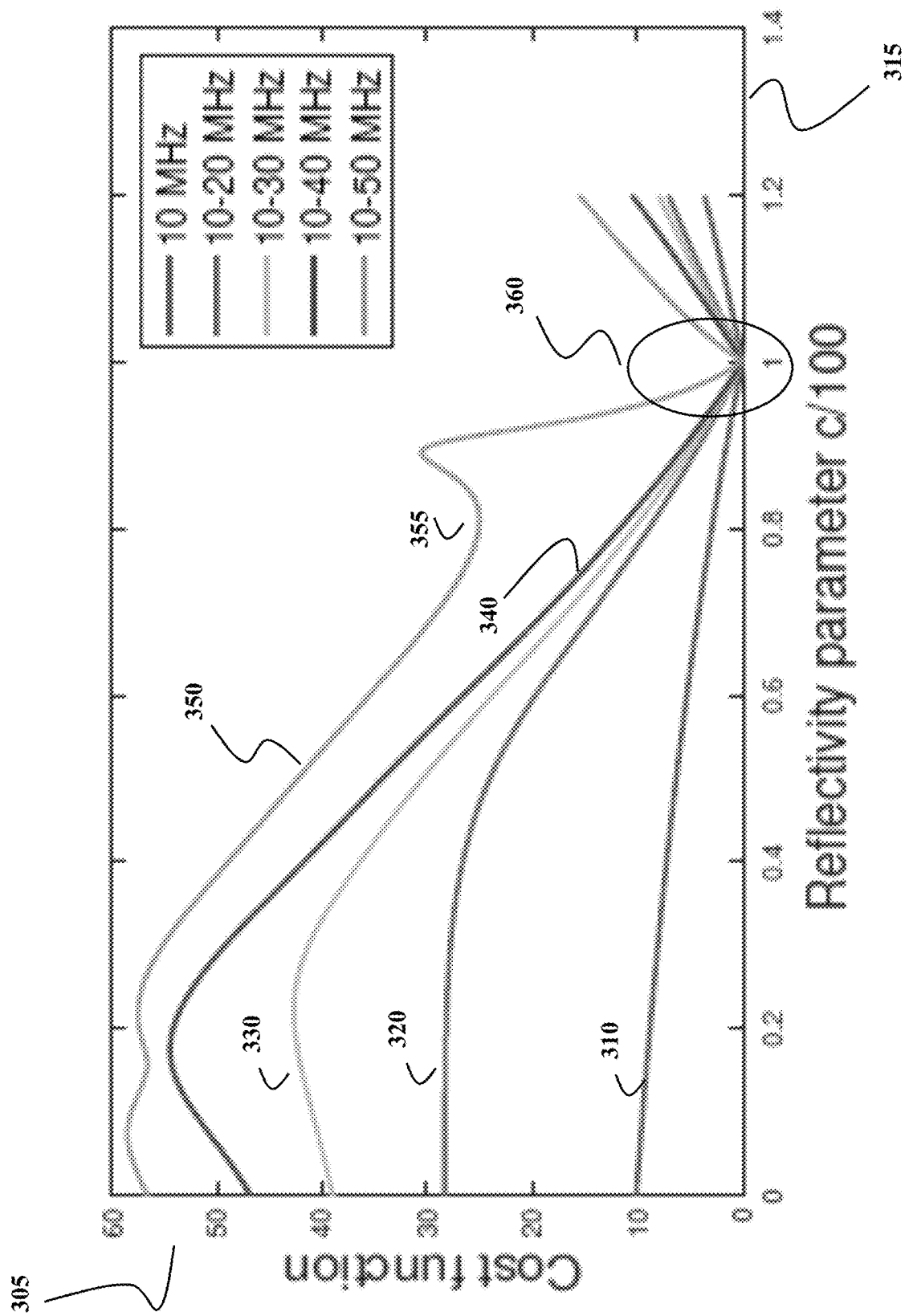
FIG. 3 shows a schematic of principles of an incremental frequency inversion method according to some embodiments.

FIG. 3 shows a schematic of principles of an incremental frequency inversion method according to some embodiments. The incremental frequency inversion method recursively reconstructs an image of the internal structure of the object until a termination condition is met. For a current iteration, the method adds a frequency to a previous set of frequencies used during a previous iteration to produce a current set of frequencies and reconstructs a current image of the internal structure of the object that minimizes a cost function 305 indicative of a difference between a portion of the scattered wavefield measured at the current set of frequencies and a wavefield synthesized from the current image. At the global minima 350, the minimized function 305 produces the reflectivity parameters 315 of the image of the internal structure of the material. However, the cost function has a complicated shape (much more complicated that in the simplified example of FIG. 3). Hence, the minimization of the cost function can produce not the global minimum 360, but one of a number of local minima 355. The incremental frequency inversion helps to address this problem.

For example, the set of frequencies includes frequencies, 10, 20, 30, 40, and 50 MHz. During the first iteration, the image is reconstructed by minimizing a cost function 310 only for the frequency of 10 MHz. For such a frequency, the reconstruction is more likely to find the global minimum 360. Next, the method adds frequency higher than any frequency in the previous set of frequencies. For example, the method adds a frequency of 20 MHz, and minimizes the cost function 320 for joint frequencies of 10 and 20 MHz in the neighborhood of the minima corresponding to the function 310. Next, the method adds a frequency of 30 MHz and minimizes the cost function 330 for joint frequencies of 10, 20 and 30 MHz in the neighborhood of the minima corresponding to the function 320. Similarly, the method adds frequencies of 40 MHz to minimize the cost function 340, and finally adds all frequencies 10-50 Mhz to together to minimize the function 350 to find the global minimum 360 corresponding to the final image.

In such a manner, frequencies are added incrementally to the inverse scattering problem. In addition, a previous image determined during the previous iteration initializes the reconstruction of the current image. This initialization incrementally guides the solution of the inverse scattering problem toward a global minimizer.

The incremental frequency inversion method does not require a smooth initial model of the image to be reconstructed. In contrast, the incremental frequency inversion method derives such a model from low frequency measurements. In effect, the incremental frequency inversion method allows to reconstruct an image of the internal structure of the object with a practical resolution and accuracy without a necessity for using prior information about the image.

Frequency Inversion

Some embodiments formulate the image reconstruction problem as a frequency inversion problem solved by incremental frequency inversion method. This rationale is based on scattering model that describes the relation between the scattered wavefield and the medium parameters. The scattering model allows to formulate the discrete inverse problem to reconstruct the medium from the set of measured reflections of the scattered wavefield.

Specifically, a wave-equation governs the acoustic or electromagnetic scattering from an inhomogeneous medium in the time domain. An equivalent representation in the frequency domain is the scalar Helmholtz equation. The integral form of the Helmholtz equation is the scalar Lippmann-Schwinger equation. Let $u_{sc}: \Omega \to \mathbb{C}$ be the scattered wavefield inside a spatial domain, or region of interest, $\Omega$, let $f: \Omega \mathbb{R}$ be the medium parameters and denote by $g: \Omega \to \mathbb{C}$ the free-space Green's function. The scalar Lippman-Schwinger scattering equation is then defined as follows $$u_{sc}(x)=u_{in}(x)+k^2\int_\Omega g(x-r)u_{sc}(r)f(r)dr, \forall x\in\Omega \quad (1)$$

where, $u_{in}$ is the input wavefield 135 generated by the transmitter 130, and $k=2\pi/\lambda$ is the wavenumber with $\lambda$ denoting the wavelength. The medium parameters, $f(x)=(\varepsilon(x)-\varepsilon_b)$, is the relative permittivity, where $\varepsilon(x)$ is the permittivity of the object and $\varepsilon_b$ is the permittivity of the background, which is assumed to be the vacuum ($\varepsilon_{vacuum}=1$).

The free-space Green's function for the Helmholtz equation $(\nabla^2+k^2)g=\delta$ is given by:

$$g(x) \triangleq \begin{cases} -\dfrac{i}{2k}e^{-ikr} & d=1 \\ -\dfrac{i}{4}H_0^{(2)}(kr) & d=2 \\ \dfrac{1}{4\pi r}e^{-ikr} & d=3 \end{cases}$$

where $r=\|x\|$, $H_0^{(2)}$ is the zero-order Hankel function of second kind, and d is the dimension of $\Omega$. The scattered wavefield is then measured 255 at the receivers 130 resulting in the following data equation:

$$y(x)=\int_\Omega h(x-r)f(r)u_{sc}(r)dr, \forall x\in\Gamma, \quad (2)$$

where $h: \Omega \to \mathbb{C}$ denotes the Green's function of the receiver and $\Gamma$ is the receiver domain. The forward problem involves computing the synthesized reflections 220 y given the input wavefield 135 $u_{in}$, medium parameters 165 f, and the Green's functions g and h.

In the discrete setting, the scattering equation and data equation reduce to the following system of linear equations for each transmitter illumination and wave number:

$$u=v+G\text{diag}(f)u,$$

$$y=H\text{diag}(f)u, \quad (3)$$

where $u\in\mathbb{C}^N$ and $v\in\mathbb{C}^N$ are the scattered 585 and input wavefields 135, respectively, N denotes the number of gridpoints used to discretize the domain $\Omega$, $f\in\mathbb{R}^N$ denotes the medium parameters 265, while $G\in\mathbb{C}^{N\times N}$ and $H\in\mathbb{C}^{n_{rec}\times N}$ are the Green's functions of the domain and receivers, respectively. Let $n_{rec}$ be the number of receivers that discretizes the receiver domain $\Gamma$, then $y\in\mathbb{C}^{n_{rec}}$ is the noise-free scattered wavefield measured 255 at the receivers 130.

The forward problem involves estimating the scattered wavefield 585 u by inverting the matrix 565 A:=I−G diag(f), where I denotes the identity operator. As the discretization dimension N increases, explicitly forming the matrix A and its inverse becomes prohibitively expensive. Therefore, a functional form of A along with the conjugate-gradient method (CG) can be used to perform the inversion. The convergence of CG depends on the conditioning of the operator A, which become ill-conditioned for large wavenumber and highly scattering medium, i.e., large value of $\|f\|_\infty$.

Figure 4A:
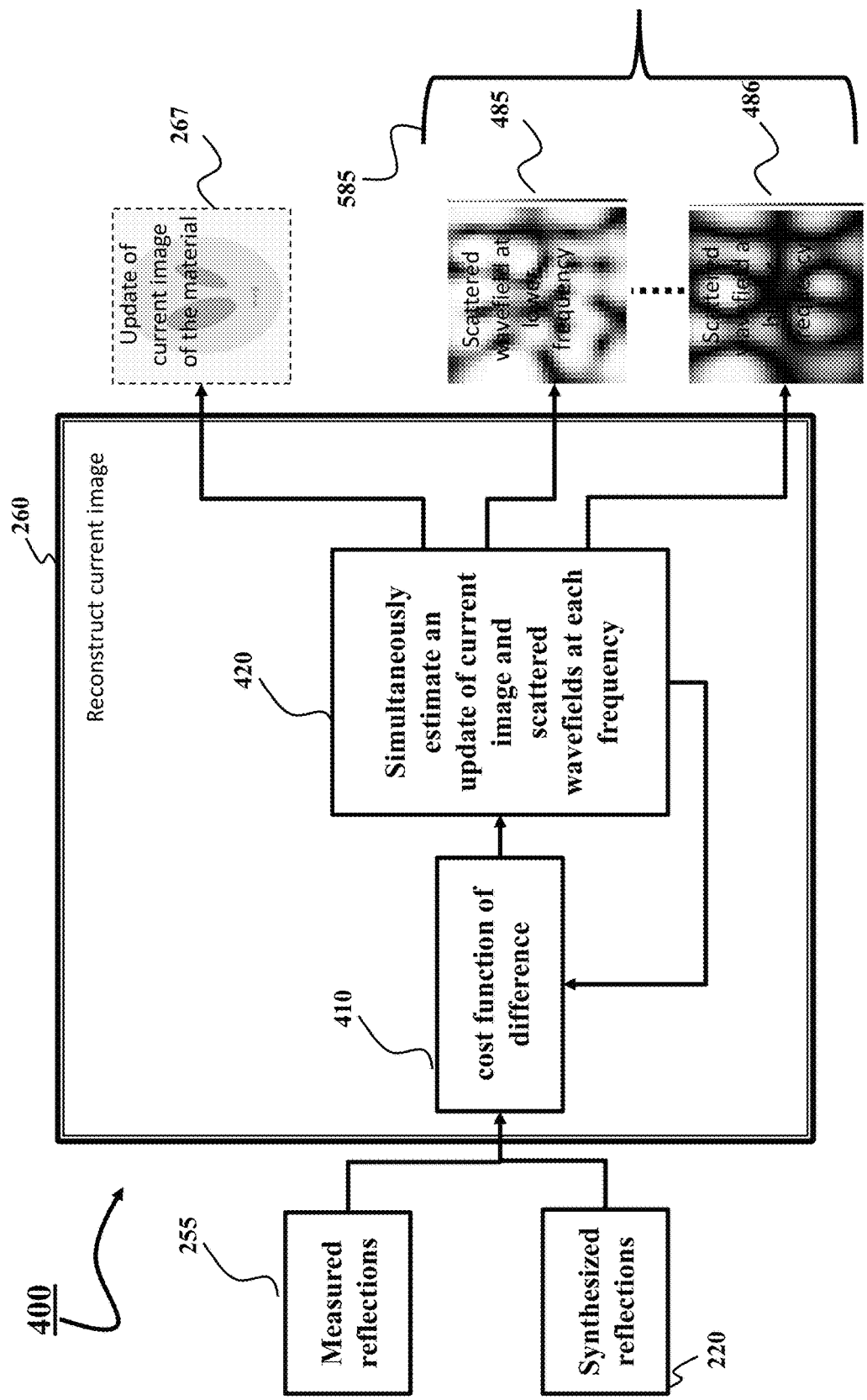
FIG. 4A shows a block diagram of a method 400 for reconstructing 260 a current image 265 for different frequencies according to some embodiments.

FIG. 4A shows a block diagram of a method 400 for reconstructing 260 a current image 265 for different frequencies according to some embodiments. The method 400 is executed multiple times for different combinations of frequencies. For example, in one iteration, the method 400 is executed to reconstruct an image 265 by minimizing a cost function 320 for two frequencies 10 and 20 MHz in the current set of frequencies. In the next iteration, the method 400 is invoked to update the image 265 for frequencies 10, 20, and 30 MHz by minimizing the cost function 330. In this iteration, the image 265 is updated based on the previous reconstruction of the image 265 resulted from minimizing the cost function 320.

Given the current estimate of the image, synthesized reflections 220 are generated and compared to the measured reflections 255. Both the synthesized reflections 220 and the measured reflections 255 are determined for the current set of frequencies 235. A difference between the synthesized reflections 220 and the measured reflections 255 is then minimized by simultaneously updating 420 the current image 265 as well as estimates of the scattered wavefields 485-486, 585 at each frequency in the current set of frequencies 235. The updated current image 265 and scattered wavefields 485-486 are in turn used to minimize 410 the cost function of the difference between the synthesized and measured reflections. In some implementations, the cost function is minimized by simultaneously estimating the current image 265 and scattered wavefields 485-486,585 at each frequency according to principles of disjoint-state method. The minimized metric of the cost function can be selected from one or a combination of a Euclidean distance between the measured reflections and synthesized reflections, a one norm distance between the measured reflections and synthesized reflections, and a summation of Euclidean distance and a barrier function, wherein the barrier function penalizes updating the image of the refractive indices of the material that have negative refractive indices and the barrier function is a summation of an exponential function taken to a negative power of every refractive index in the image of the refractive indices of the material.

Figure 4B:
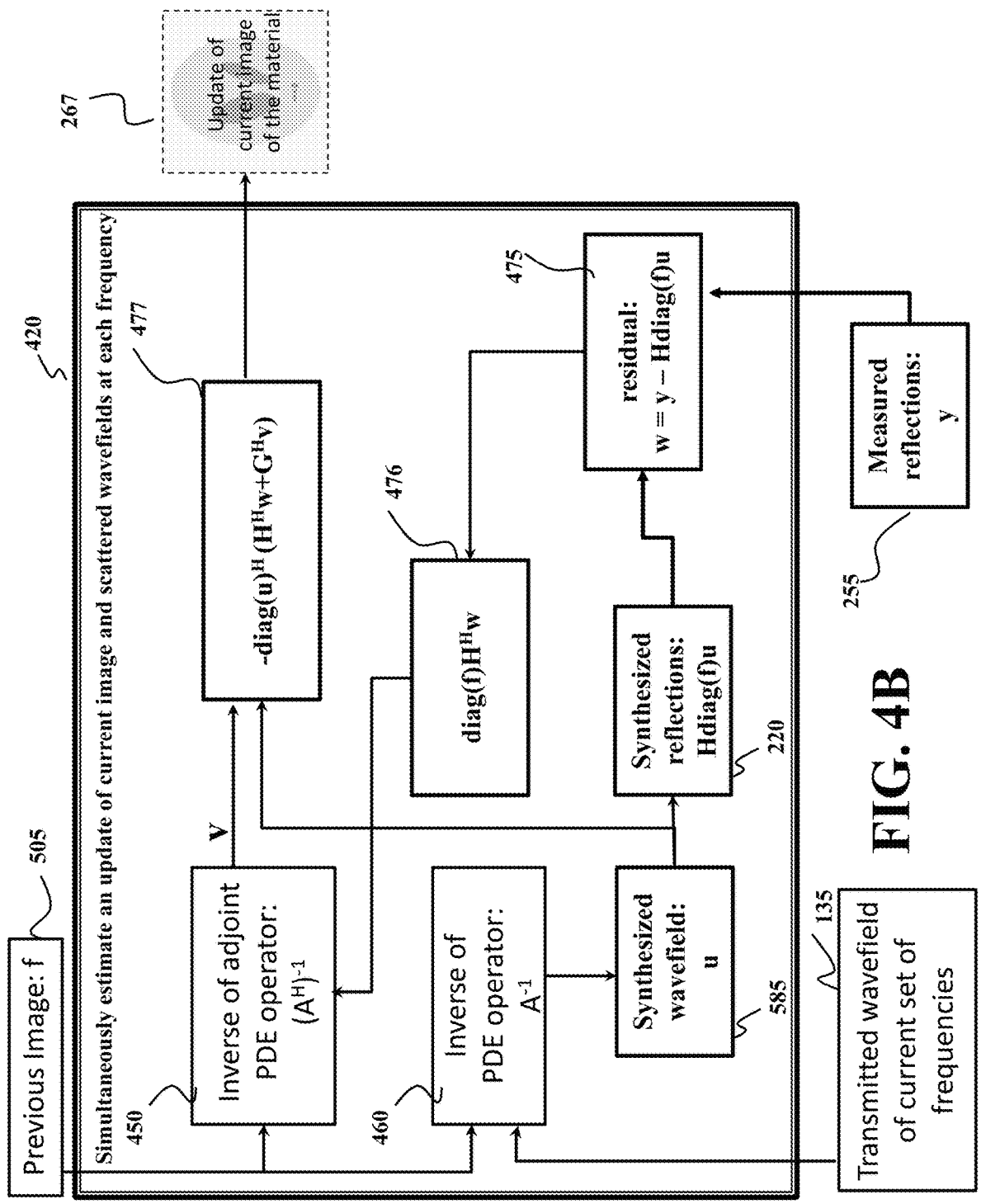
FIG. 4B shows a block diagram of a method for computing an update of the image of the object as well as computing an estimate of the scattered wavefield based on an adjoint state method according to one embodiment.

FIG. 4B shows a block diagram of a method for computing an update of the image of the object as well as computing an estimate of the scattered wavefield based on an adjoint state method according to one embodiment. The embodiment uses the simultaneous estimation of the update of the current image and the scattered wavefields at each frequency. The block diagrams describe the details of the adjoint state method that is used to compute an update of the image of the structure of the object by incorporating the gradient of the resulting scattered wavefield into the update equation of the image of the structure of the object. This cross dependency between the image of the structure of the object and the resulting scattered wavefield makes the adjoint state method necessary to find an appropriate update for the image of the structure of the object and avoid bad local minima for the problem.

After the first iteration of execution of the method 400, the current reconstruction of the image 265 is initialized by the image of the internal structure of the object determined during a previous iteration. Such an initialization allows to avoid local minima in cost function minimization. For example, in some embodiments the method 400 is initialized in the first iteration by setting the previous image to be an all zero image, i.e. free space material. In another embodiment, the previous image is set to a prior assumption on the material of the object provided by an expert.

Figure 5:
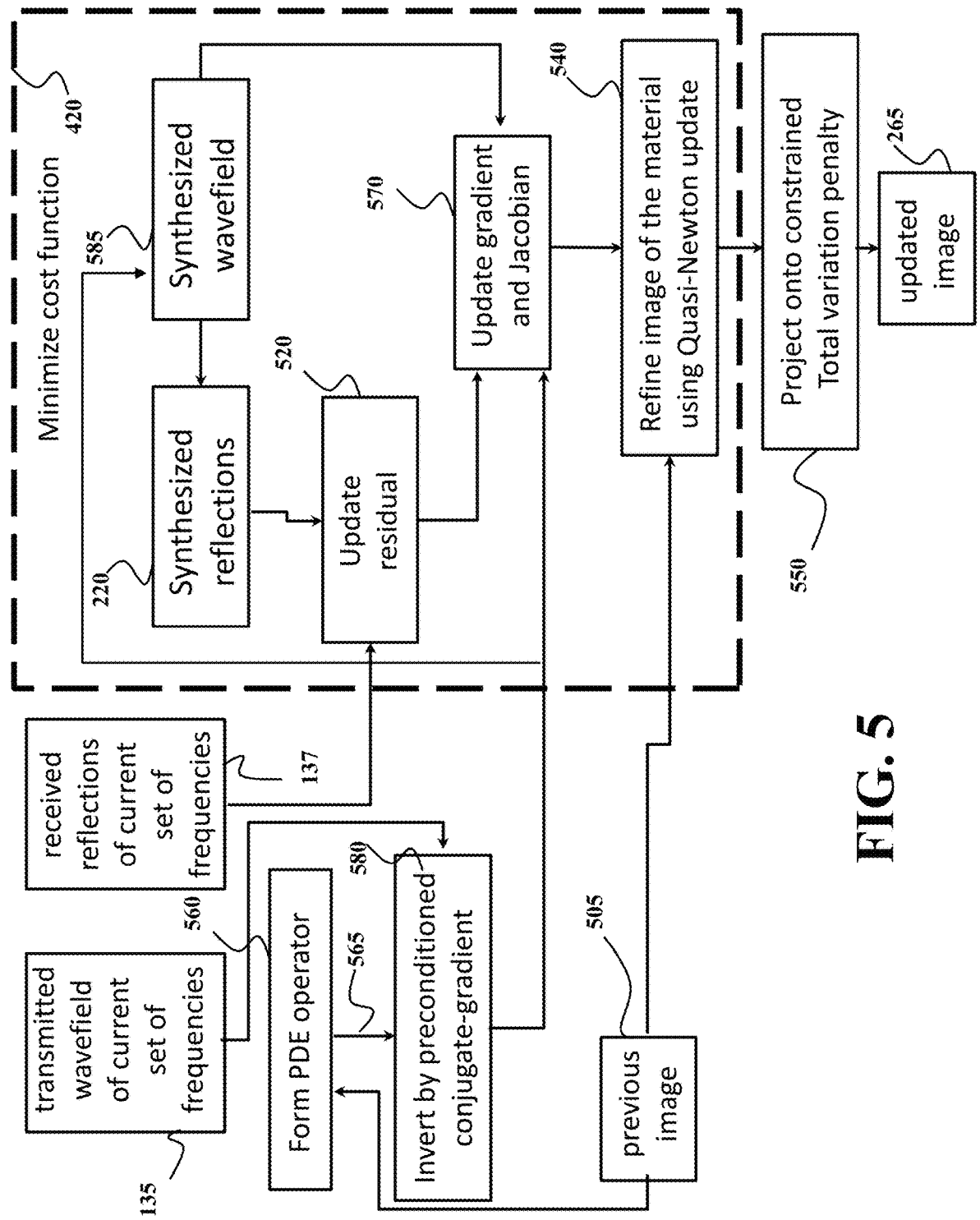
FIG. 5 shows a block diagram of a method for updating the image of the distribution of permittivity of a material for a current set of frequencies according to one embodiment.

FIG. 5 shows a block diagram of a method for updating the image of the distribution of permittivity of a material for a current set of frequencies according to one embodiment. The embodiment forms an operator 560 that discretizes a partial differential equation (PDE) such that the operator 560 characterizes the interaction between a transmitted pulse 135 and a previous estimate of the image of the distribution of permittivity of the material 505 at all frequencies in the current set of frequencies 235. The PDE operator is determined such that the product of the PDE operator with the correct scattered wavefields is equal to the transmitted pulse. Therefore, given the previous image 505 determined during a previous iteration and a portion of the transmitted wavefield 135 for the current set of frequencies, the PDE operator is inverted 580 using a preconditioned conjugate-gradient method in order to estimate the scattered wavefields 585. The measured/received reflections 137 are then compared with the synthesized reflections 220 to update 520 a residual. The residual is used to update 570 a gradient and Jacobian of the image according to an adjoint state procedure. The image is then updated using a Quasi-Newton update 540 and the result is projected onto a constrained total variation penalty function 550 to update the image 265.

Inverse Problem

An inverse scattering problem is defined as the estimation of medium parameters given the measured reflections 255 of scattered wavefield at $n_{rec}$ receivers 130 for each input wavefield 135 generated from $n_t$ transmitters 130. In the discrete setting and assuming that measurements are contaminated by white Gaussian noise, the inverse problem is as follows:

$$\min_{f,u} \sum_{j=1}^{n_f} \sum_{i=1}^{n_t} \frac{1}{2} \|y_{ij} - H_j \text{diag}(f) u_{ij}\|_2^2, \quad (4)$$

$$\text{s.t.} \quad (I - G_j \text{diag}(f)) u_{ij} = v_{ij} \; \forall \; i, j,$$

where $n_f$ are the total number of frequencies in the complete set of frequencies 150, and $y_{ij}$ is the noisy measured reflections 255 received at $n_{rec}$ receivers from transmitter i at frequency j.

Let $\Pi = \{f^a, u^a\}$ denote the solution set of the problem (4). In general, problem (4) is ill-posed and admits multiple solutions, i.e., $|\Pi| > 1$. Therefore, spatial regularization in the form of a penalty function 280 $\mathcal{R}(f)$ can be added to reduce the solution space. The regularized problem is then represented as $$\min_{f,u} \sum_{i,j} \mathcal{D}_{ij}(f, u_{ij}) + \mathcal{R}(f), \quad (5)$$

$$\text{s.t.} \quad (I - G_j \text{diag}(f)) u_{ij} = v_{ij} \; \forall \; i, j,$$

where, $\mathcal{D}_{ij}$ represents the data-fidelity term or cost function 410 for transmitter i at frequency j.

The least-squares cost function 410 in (5) provides a natural separation across frequencies. Moreover, the topology of the nonconvex cost function varies drastically between frequencies and can be leveraged to find a sequence of local minima that gradually lead to the global minimizer of the problem. As higher frequency wavefields are introduced, the cost function starts to exhibit many local minima that are farther away from the global minimizer compared to the low-frequency wavefields.

Some embodiments use the observations above to design an incremental frequency inversion framework where the model of the object's permittivity 265 is sequentially updated as higher frequencies are included in the inversion. Given a measured reflections containing a set 150 of $n_f$ frequency components indexed in increasing order from 1 to $n_f$, the incremental frequency inversion framework iteratively estimates the image of the object model 265 from low to high-frequency while keeping the low-frequency cost function as a regularizer for high-frequency inversions:

$$\text{for } k = 1, \ldots, n_f:\qquad(6)$$

$$(f^k, u^d) \triangleq \underset{f,u}{\operatorname{argmin}} \left\{ \mathcal{D}_k(f, u_k) + \sum_{j=1}^{k-1} \lambda_j \mathcal{D}_j(f, u_j) + \mathcal{R}(f) \right.$$

$$\left. \text{s.t. } (I - G_j \operatorname{diag}(f)) u_{ij} = v_{ij} \; \forall \; i, j \right\},$$

where $\mathcal{D}_j(f, u_j) = \Sigma_{i=1}^{n_t} \mathcal{D}_{ij}(f, u_{ij})$, and $\lambda_j \in (0,1]$ are regularization parameters that control the impact of the low-frequencies cost functions with respect to the $k^{th}$-frequency cost function. Therefore, instead of solving a single non-convex minimization problem in (5), some embodiments solve $n_f$ subproblems 260 sequentially according to (6), where the sequence of solutions moves us closer to the global minimizer of (5).

To solve the minimization problem in (6), one embodiment uses a proximal Quasi-Newton method 540. The embodiment first computes the gradient 267 of the function $$\mathcal{F}(f, u) \triangleq \mathcal{D}_k(f, u_k) + \sum_{j=1}^{k-1} \lambda_j \mathcal{D}_j(f, u_j)$$

with respect to f 265, with the wavefield u 235 satisfying the PDE constraints. Such gradient computation is performed using an adjoint-state method to simultaneously estimate 420 current image and scattered wavefields at each frequency. A descent direction is then obtained by forming an approximation to the Hessian using limited memory BFGS 540. A $(t+1)^{th}$-iterate of the model is then given by $$f^{(t+1)} \triangleq P_{TV \leq \tau}(f^{(t)} - \gamma_t \tilde{H}^{-1} \nabla_f \mathcal{F}(f^{(t)}, u)),$$

where $\gamma_t$ is a step length computed using backtracking line-search, $\tilde{H}$ is an L-BFGS Hessian, and $\mathcal{P}_{TV \leq \tau}(\bullet)$ 550 is a proximal operator for the TV-norm constrained by $\tau$ 610. For each frequency batch in (6), we keep updating the model till the norm of the gradient diminishes to a small value.

Total-Variation Regularization

Formally, the Total-Variation (TV) norm for a function u: $\Omega \to \mathbb{R}$ is represented with the help of bounded function $\phi$ as
$TV(u) \triangleq \sup\{u(x) \quad \operatorname{div} \quad \phi dx : \phi \in C_c^1(\Omega, \mathbb{R}^d),$
$\|\phi\|_\infty \leq 1\} = \int_\Omega |\nabla u(x)| dx = \|\nabla u(x)\|_1.$ This norm measures the total change in the derivative of the function over a finite domain. As a result, regularization with a TV norm promotes piecewise constant approximation of the true model.

Some embodiments use the TV regularization in its constrained form 550, such that, $$\mathcal{R}_{TV}(f) \triangleq \delta(TV(f) \leq \tau),\qquad(7)$$

where $\delta(\bullet)$ is an indicator function, and $\tau$ is a constraint parameter 610. Let D be the finite difference operator that discretizes the gradient, then $TV(f) = \|Df\|_1$. In order to impose the TV norm constraint, one embodiment defines the proximal operator:

$$\mathcal{P}_{TV \leq \tau}(w) \triangleq \underset{f}{\operatorname{argmin}} \left\{ \frac{1}{2} \|f - w\|_2^2 + \mathcal{R}_{TV}(f) \right\}\qquad(8)$$

which can be evaluated using the alternating direction method of multipliers (ADMM), as shown in Algorithm 1.

| Algorithm 1 Proximal for constrained TV regularization |
|---|
| Input $w \in \mathbb{R}^n$, $D \in \mathbb{R}^{m \times n}$, $\tau > 0$, $\rho > 0$, $t_{max}$, $\gamma \in (0, 1]$ |
| Output $f^{(t_{max})}$ |
| 1:      $f^{(0)} = w^{(k)}$, $z^{(0)} = 0$, $\lambda^{(0)} = 0$ |
| 2:      for t = 0 to $t_{max}$ do |
| 3:          $f^{(t+1)} := (I - \rho D^T D)^{-1} (w + D^T (z^{(t)} - \lambda^{(t)}))$ |
| 4:          $z^{(t+1)} := \mathcal{P}_{\|\cdot\|_1 \leq \tau}(Df^{(t+1)} + \lambda^{(t+1)})$ |
| 5:          $\lambda^{(t+1)} := \lambda^{(t)} + \gamma (Df^{(t+1)} - z^{(t+1)})$ |
|           check termination conditions |
| 7:      end for |
| 8:      return $f^{(t_{max})}$ |

FIG. 6 shows a block diagram of a method for updating an upper bound 610 $\tau$ on a total variation penalty function according to one embodiment. From the previous image 505, the total variation penalty function is evaluated to initialize the upper bound 610 on the penalty function. The previous image 505 is also used to estimate the synthesized scattered wavefield 585 at the current set of frequencies by multiplying the inverse of the PDE operator A by the incident wavefield 135. The upper bound needs to be updated by incorporating information from the received reflections at the current set of frequency coefficients. From the current synthesized wavefields 585 corresponding to the previous image 505, a difference is computed 620 between the residual r is then used to compute 630 a squared Euclidean distance on the one hand, and is also multiplied 640 by the adjoint of the forward operator H on the other hand to produce a vector $z = H^T r$. A polar function of the total variation penalty is applied 650 to the vector z. The polar function is defined as the two-infinity mixed norm of the vector Dz, where D is the discretized gradient operator. The result is then used to divide the squared Euclidean distance for the difference. The resulting amount is then added 670 to the initial value of the upper bound to produce the updated upper bound 675.

Figure 7A:
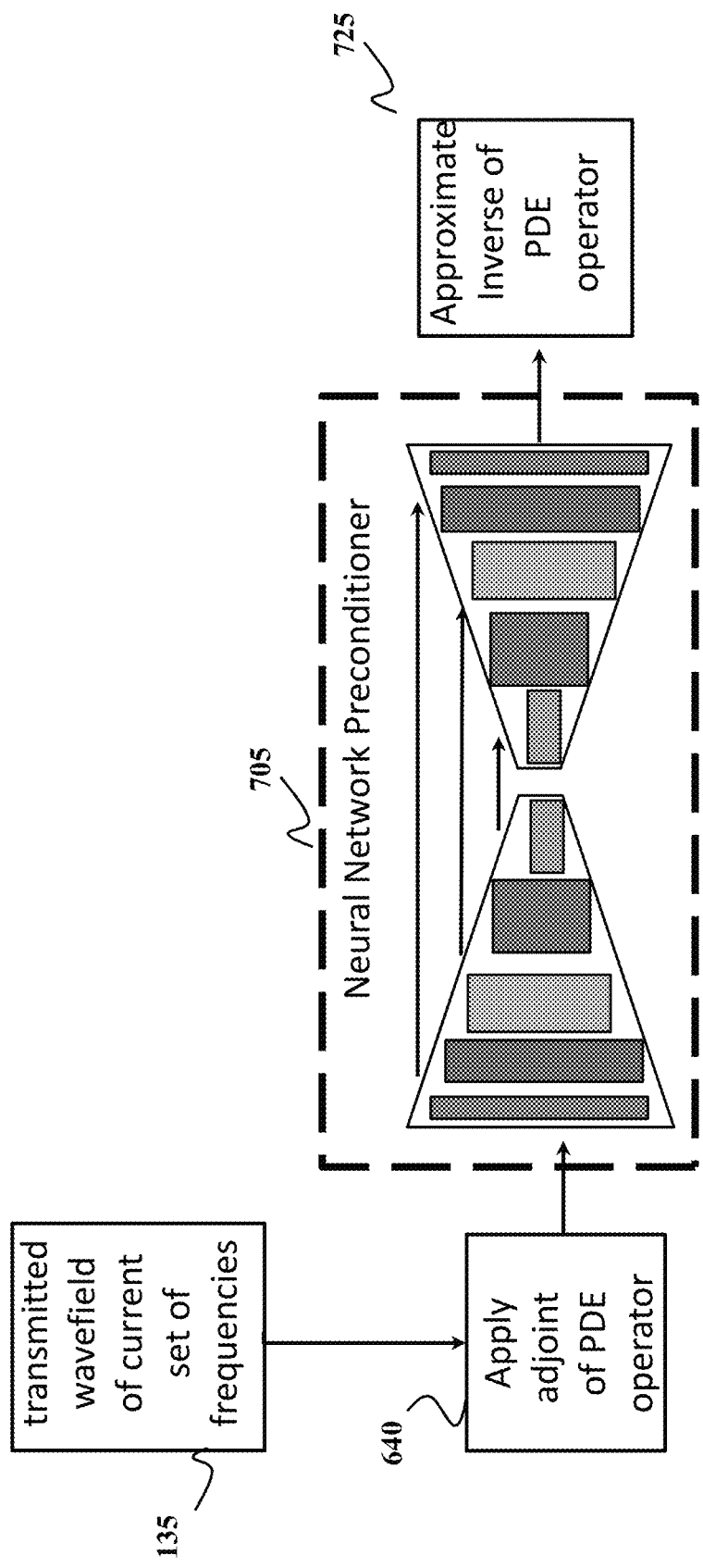
FIG. 7A shows a schematic of a neural network-based preconditioner used by one embodiment to compute a preconditioner before inverting the PDE operator.

FIG. 7A shows a schematic of a neural network-based preconditioner used by one embodiment to compute a preconditioner for inverting the PDE operator. This embodiment improves computational efficiency of inverse reconstruction. The computation of a preconditioner is non-trivial and can be computationally very expensive. Therefore, the embodiment trains a deep neural network 705 with a U-net architecture. The U-shape of the U-net architecture skips connections between layers of the same dimensions in order to compute a fast preconditioner to the PDE operator in presence of noise. The deep neural network-based preconditioner is trained for a specific dimension of the image that is to be estimated and for a specific configuration of transmitting and receiving antennas. Moreover, the neural network is trained to approximate the inverse of the PDE operator 725 by taking as input the transmitted wavefield 135 and applying the adjoint of the PDE operator 640 that is defined by assuming any image of the material, and outputting an estimate of the scattered wavefields 585.

Figure 7B:
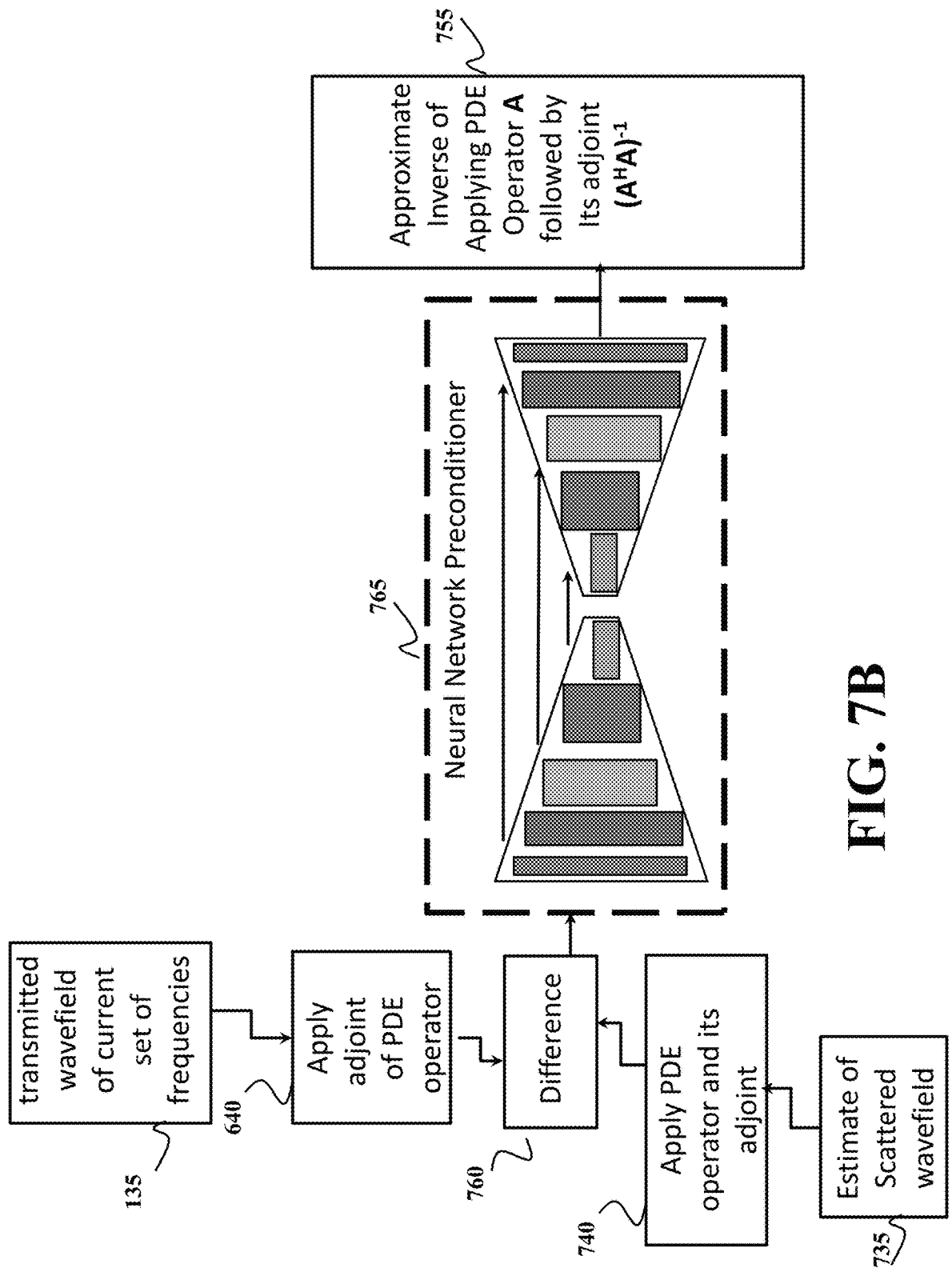
FIG. 7B is a schematic of an incremental frequency inversion method with a neural network-based preconditioner according to some embodiments.

FIG. 7B is a schematic of an incremental frequency inversion method with a neural network-based preconditioner 765 according to some embodiments. In this embodiments, the preconditioner is used within an inversion such conjugate gradient to speed up the convergence of the method. The network is designed to have a U-shape architecture. For a specific PDE operator A, and is trained to compute the inverse 755 of $(A^H A)^{-1}$ applied to the residual $A^H v - A^H Au$. The residual is obtained by applying 640 an adjoint of a PDE operator to a transmitted wavefield 135 to produce $A^H v$. An estimate of the scattered wavefield 735 is also processed by applying 740 the PDE operator and its adjoint to produce $A^H Au$. A difference 760 is then computed between $A^H v$ and $A^H Au$, and the result is input to the neural network.

Figure 8:
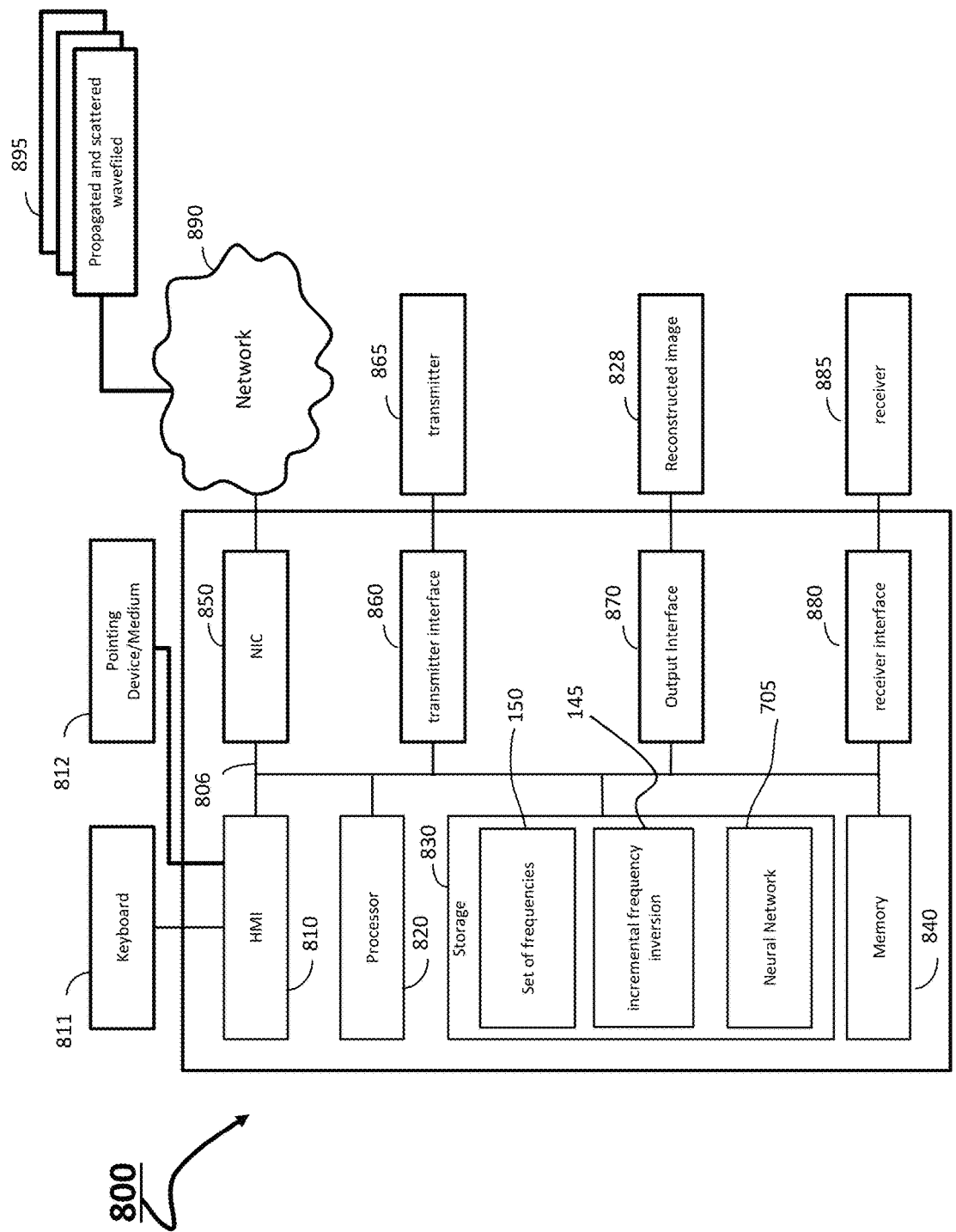
FIG. 8 shows a block diagram of a tomographic imaging system 800 in accordance with some embodiments.

FIG. 8 shows a block diagram of a tomographic imaging system 800 in accordance with some embodiments. The tomographic imaging system 800 can have a number of interfaces connecting the system 800 with other systems and devices. A network interface controller 850 is adapted to connect the system 800 through the bus 806 to a network 890 connecting the tomographic imaging system 800 with sensing devices. For example, the tomographic imaging system 800 includes a transmitter interface 860 configured to command to a transmitter 865 to emite a pulse wave 135. Using a receiver interface 880 connected to a receiver 885, the system 800 can receive the reflections 137 of the scattered wavefield corresponding to the transmitted pulse 135. In some implementations, the tomographic imaging system 800 receives the information 895 about scattered wavefield 137 and transmitted pulse 135 through the network 890, The tomographic imaging system 800 includes an output interface 870 configured to render the reconstructed image 828. For example, the output interface 870 can display the reconstructed image 828 on a display device, store the image into storage medium and/or transmit the image over the network. For example, the system 800 can be linked through the bus 806 to a display interface adapted to connect the system 800 to a display device, such as a computer monitor, camera, television, projector, or mobile device, among others. The system 800 can also be connected to an application interface adapted to connect the system to equipment for performing various tasks.

In some implementations, the tomographic imaging system 800 includes an input interface to receive measurements at a set of frequencies of a wavefield scattered by an internal structure of an object. Examples of the input interface include NIC 850, the receiver interface 880, and a human machine interface 810. The human machine interface 810 within the system 800 connects the system to a keyboard 811 and pointing device 812, wherein the pointing device 812 can include a mouse, trackball, touchpad, joy stick, pointing stick, stylus, or touchscreen, among others.

The system 800 includes a processor 820 configured to execute stored instructions 830, as well as a memory 840 that stores instructions that are executable by the processor. The processor 820 can be a single core processor, a multi-core processor, a computing cluster, or any number of other configurations. The memory 840 can include random access memory (RAM), read only memory (ROM), flash memory, or any other suitable memory systems. The processor 820 can be connected through the bus 806 to one or more input and output devices.

The instructions 830 can implement a method for incremental frequency inversion 145. The instructions can also include the trained neural network 705 for determining a preconditioner of the frequency inverse problem and a set of frequencies 150 for the incremental frequency inversion 145.

Various embodiments are suitable for two acquisition modes in inverse scattering: transmission mode, where the transmitters and receivers are located on opposite sides of the material, and reflection mode, where the transmitters and receivers are located on the same side of the object. The reflection setup generally arises due to a limitation that allows accessing only one side of the material, as in the case of underground imaging. To that end, the reflection setup is effective in some applications, but results in the reflection tomography scenario where the inverse scattering problem is severely ill-posed since the measured reflections contain far less spatial frequency information about the object. To that end, it is an object of one embodiment to provide method and system suitable for reflection tomographic imaging.

Figure 9:
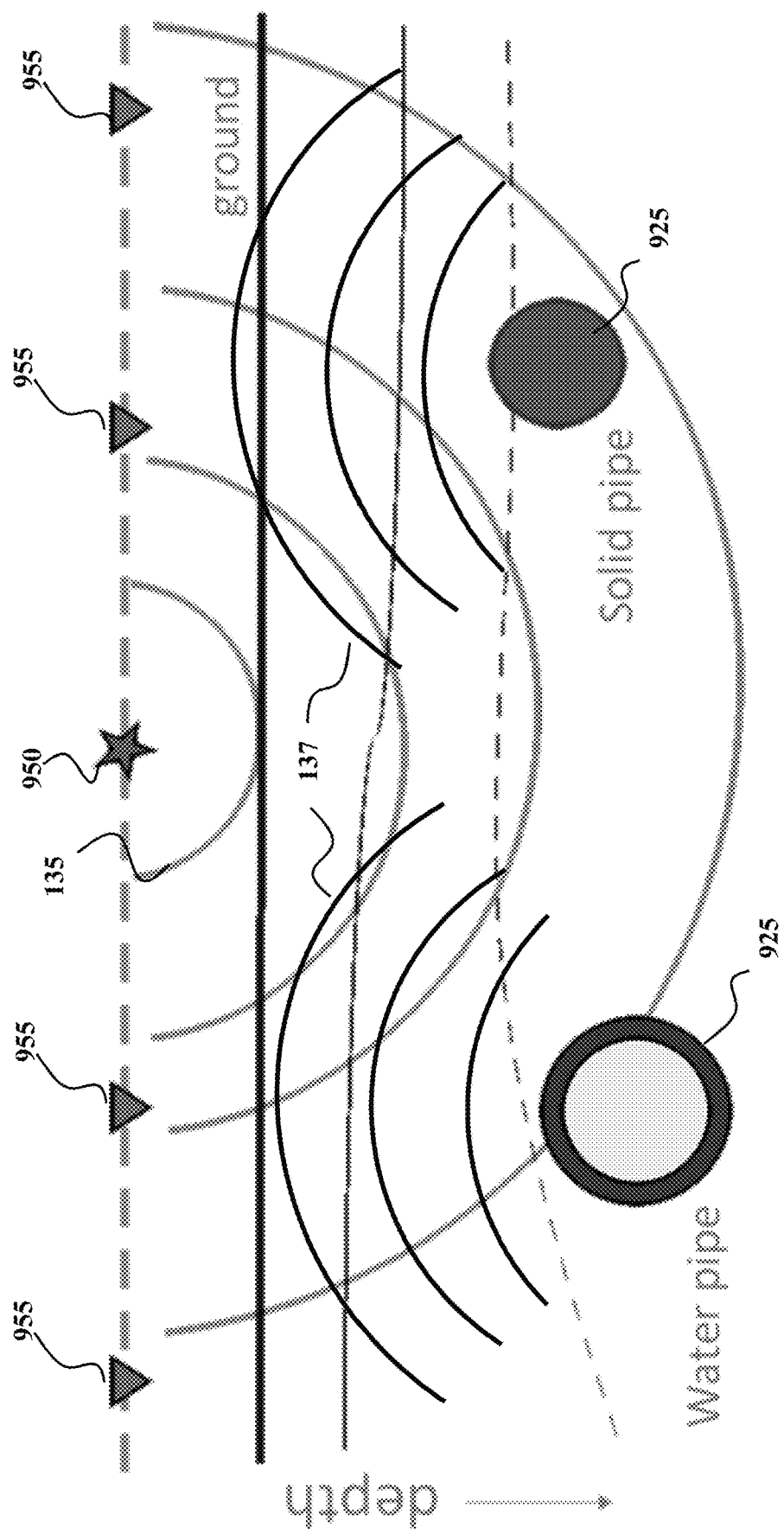
FIG. 9 shows an exemplar schematic of a reflection setup according to one embodiment.

FIG. 9 shows an exemplar schematic of a reflection setup according to one embodiment. This embodiment is specific to a sensing setup for imaging underground infrastructure. A transmitting antenna 950 and several receiving antennas 955 are positioned above the ground. The transmitting antenna 950 emits a pulse 135 that propagates through the ground layer until it interacts with infrastructure components such as a water pipe 925 or a solid structural beam or pipe 925 causing multiple wave scattering events. The interaction between the transmitted pulse and the infrastructure components results in reflected wavefields 137. The embodiment reconstructs the image of underground infrastructure using the incremental frequency inversion method 145.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Though, a processor may be implemented using circuitry in any suitable format.

Also, the embodiments of the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Although the invention has been described by way of examples of preferred embodiments, it is to be understood that various other adaptations and modifications can be made within the spirit and scope of the invention.

Therefore, it is the object of the appended claims to cover all such variations and modifications as come within the true spirit and scope of the invention.

We claim:

1. A tomographic imaging system, comprising
an input interface to receive measurements at a set of frequencies of a wavefield scattered by an internal structure of an object;
a processor configured to recursively reconstruct an image of the internal structure of the object until a termination condition is met, wherein, for a current iteration, the processor is configured to add a frequency to a previous set of frequencies used during a previous iteration to produce a current set of frequencies, wherein the added frequency is higher than any frequency in the previous set of frequencies; and reconstruct a current image of the internal structure of the object that minimizes a difference between a portion of the scattered wavefield measured at the current set of frequencies and a wavefield synthetized from the current image, wherein a previous image determined during the previous iteration initializes the reconstruction of the current image, wherein to reconstruct the current image the processor is configured to determine simultaneously an update of the current image of the internal structure of the object and an estimate of the scattered wavefield inside the object having the structure corresponding to the current image at each frequency in the current set of frequencies to minimize a sum of the differences between measured reflections and synthesized reflections of the reconstructed scattered wavefield for each frequency in the current set of frequencies, wherein to determine simultaneously the current image of the internal structure of the object and an estimate of the scattered wavefield inside the object the processor is configured to determine an estimate of the scattered wavefield based on a current estimate of the image of the internal structure of the object by simulating an interaction between a probing pulse and the scattered wavefield resulted by scattering the probing pulse with material inside the object;

determine an estimate of an adjoint scattered wavefield that compensates for a residual error between the measured reflections and the synthesized reflections of the reconstructed scattered wavefield; and compute an update of the current image of the internal structure of the object by combining the estimate of the scattered wavefield, the estimate of the adjoint scattered wavefield, and the residual error between the measured reflections and the synthesized reflections of the reconstructed scattered wavefield using an adjoint state equation; and an output interface configured to render the reconstructed image.

2. The system of claim 1, wherein the reconstructed image is an image of refractive indices of material inside the object.

3. The system of claim 1, wherein the reconstructed image includes distribution of permittivity of material inside the object.

4. The system of claim 1, further comprising:

a set of transmitters, each transmitter is configured to transmit a probing pulse into the object, wherein each pulse is an electromagnetic wave or an acoustic wave that occupies a frequency band including the set of frequencies; and a set of receivers configured to measure, at each frequency from the set of frequencies, one or combination of reflections and refractions of propagation of the probing pulses through the object to produce the measurements of the wavefield.

5. The system of claim 4, wherein the transmitters and the receivers are located on the same side of the object, such that the system operates in a reflection mode.

6. The system of claim 1, wherein unique frequencies in the set of frequencies are ordered from the lowest frequency to the highest frequency forming an ordered set of frequencies, wherein for each iteration, the processor adds to the previous set of frequencies a frequency from the ordered set of frequencies with an index corresponding to a number of the current iteration, such that only the lowest frequency is processed during the first iteration, and wherein the termination condition is reaching a number of iterations that is equal to the length of the ordered set of frequencies.

7. The system of claim 1, wherein to determine simultaneously the current image and the scattered wavefields, the processor is configured to form a PDE operator that discretizes a partial differential equation (PDE) that describes an interaction between a probing pulse, the scattered wavefield resulted by scattering the probing pulse with material inside the object, and the refractive indices of the material inside the object;

invert the PDE operator given an initialized current image to determine a Jacobian of the scattered wavefield with respect to the current image of the refractive indices of the material;

update the current image of the refractive indices of the material by minimizing a cost function between the measured reflections in the set of frequency components and a synthesized scattered wavefields obtained by combining the Jacobian of the scattered wavefield and a quasi-Newton descent direction of the cost function with respect to the image of the refractive indices of the material; and project the image of the refractive indices of the material onto a constrained total variation penalty function.

8. The system of claim 7, where the cost function between the measured reflections and synthesized reflections of the reconstructed scattered wavefield in the set of frequency components includes one or a combination of a Euclidean distance between the measured reflections and synthesized reflections, a one norm distance between the measured reflections and synthesized reflections, and a summation of Euclidean distance and a barrier function, wherein the barrier function penalizes updating the image of the refractive indices of the material that have negative refractive indices and the barrier function is a summation of an exponential function taken to a negative power of every refractive index in the image of the refractive indices of the material.

9. The system of claim 7, wherein the PDE operator is inverted using a preconditioned conjugate gradient method that inverse the PDE operator using a preconditioner.

10. The system of claim 9, wherein the processor determines the preconditioner of the preconditioned conjugate gradient method using a neural network trained to estimate of the scattered wavefield from an input wavefield for each frequency in the current set of frequencies.

11. The system of claim 7, wherein the constrained total variation function is constrained by an upper bound, wherein the processor is further configured to initialize the upper bound for the current image; and update the upper bound at the start of every iteration using a Newton root-finding method that adds a ratio of the square of the Euclidean distance between the measured reflections and the synthesized reflections of the reconstructed scattered wavefield and a polar function of the constrained total variation function applied to a product of the adjoint of the PDE operator and the difference between the measured reflections and synthesized reflections of the reconstructed scattered wavefield.

12. The system of claim 11, wherein the deep learning network has a U-net architecture.

13. The system of claim 1, wherein the object includes elements of an underground infrastructure.

14. A tomographic imaging method, wherein the method uses a processor coupled with stored instructions implementing the method, wherein the instructions, when executed by the processor carry out steps of the method, comprising:

receiving measurements at a set of frequencies of a wavefield scattered by an internal structure of an object;

reconstructing recursively an image of the internal structure of the object until a termination condition is met, wherein, for a current iteration, the method comprising:

adding a frequency to a previous set of frequencies used during a previous iteration to produce a current set of frequencies, wherein the added frequency is higher than any frequency in the previous set of frequencies; and reconstructing a current image of the internal structure of the object that minimizes a difference between a portion of the scattered wavefield measured at the current set of frequencies and a wavefield synthetized from the current image, wherein a previous image determined during the previous iteration initializes the reconstruction of the current image; and rendering the reconstructed image, wherein to reconstruct the current image the processor is configured to determine simultaneously an update of the current image of the internal structure of the object and an estimate of the scattered wavefield inside the object having the structure corresponding to the current image at each frequency in the current set of frequencies to minimize a sum of the differences between measured reflections and synthesized reflections of the reconstructed scattered wavefield for each frequency in the current set of frequencies, wherein to determine simultaneously the current image of the internal structure of the object and an estimate of the scattered wavefield inside the object the method is comprising:

determining an estimate of the scattered wavefield based on a current estimate of the image of the internal structure of the object by simulating an interaction between a probing pulse and the scattered wavefield resulted by scattering the probing pulse with material inside the object;

determining an estimate of an adjoint scattered wavefield that compensates for a residual error between the measured reflections and the synthesized reflections of the reconstructed scattered wavefield; and computing an update of the current image of the internal structure of the object by combining the estimate of the scattered wavefield, the estimate of the adjoint scattered wavefield, and the residual error between the measured reflections and the synthesized reflections of the reconstructed scattered wavefield using an adjoint state equation.

15. The method of claim 14, wherein the reconstructed image includes one or combination of refractive indices of material inside the object and distribution of permittivity of material inside the object.

16. The method of claim 14, wherein unique frequencies in the set of frequencies are ordered from the lowest frequency to the highest frequency forming an ordered set of frequencies, wherein for each iteration, the method adds to the previous set of frequencies a frequency from the ordered set of frequencies with an index corresponding to a number of the current iteration, such that only the lowest frequency is processed during the first iteration, and wherein the termination condition is reaching a number of iterations that is equal to the length of the ordered set of frequencies.

17. A non-transitory computer readable storage medium embodied thereon a program executable by a processor for performing a method, the method comprising:

receiving measurements at a set of frequencies of a wavefield scattered by an internal structure of an object;

reconstructing recursively an image of the internal structure of the object until a termination condition is met, wherein, for a current iteration, the method comprising:

adding a frequency to a previous set of frequencies used during a previous iteration to produce a current set of frequencies, wherein the added frequency is higher than any frequency in the previous set of frequencies; and reconstructing a current image of the internal structure of the object that minimizes a difference between a portion of the scattered wavefield measured at the current set of frequencies and a wavefield synthetized from the current image, wherein a previous image determined during the previous iteration initializes the reconstruction of the current image; and rendering the reconstructed image, wherein to reconstruct the current image the processor is configured to determine simultaneously an update of the current image of the internal structure of the object and an estimate of the scattered wavefield inside the object having the structure corresponding to the current image at each frequency in the current set of frequencies to minimize a sum of the differences between measured reflections and synthesized reflections of the reconstructed scattered wavefield for each frequency in the current set of frequencies, wherein to determine simultaneously the current image of the internal structure of the object and an estimate of the scattered wavefield inside the object the method is comprising:

determining an estimate of the scattered wavefield based on a current estimate of the image of the internal structure of the object by simulating an interaction between a probing pulse and the scattered wavefield resulted by scattering the probing pulse with material inside the object, determining an estimate of an adjoint scattered wavefield that compensates for a residual error between the measured reflections and the synthesized reflections of the reconstructed scattered wavefield; and computing an update of the current image of the internal structure of the object by combining the estimate of the scattered wavefield, the estimate of the adjoint scattered wavefield, and the residual error between the measured reflections and the synthesized reflections of the reconstructed scattered wavefield using an adjoint state equation.

18. The medium of claim 17, wherein unique frequencies in the set of frequencies are ordered from the lowest frequency to the highest frequency forming an ordered set of frequencies, wherein for each iteration, the method adds to the previous set of frequencies a frequency from the ordered set of frequencies with an index corresponding to a number of the current iteration, such that only the lowest frequency is processed during the first iteration, and wherein the termination condition is reaching a number of iterations that is equal to the length of the ordered set of frequencies.

* * * * *